United States Patent
Laakkonen et al.

(10) Patent No.: US 10,847,010 B2
(45) Date of Patent: Nov. 24, 2020

(54) METHOD, MOBILE DEVICE AND SYSTEM FOR OPTIMIZING WAKE-UP ALARM FOR TWO OR MORE PERSONS

(71) Applicant: Oura Health Oy, Oulu (FI)

(72) Inventors: Harri Laakkonen, Oulu (FI); Hannu Kinnunen, Oulu (FI); Ashley Colley, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 16/559,780

(22) Filed: Sep. 4, 2019

(65) Prior Publication Data
US 2020/0090486 A1 Mar. 19, 2020

(30) Foreign Application Priority Data
Sep. 19, 2018 (FI) .................................... 20185777

(51) Int. Cl.
*G08B 21/04* (2006.01)
*G08B 21/06* (2006.01)
(Continued)

(52) U.S. Cl.
CPC .......... *G08B 21/06* (2013.01); *A61B 5/02055* (2013.01); *A61B 5/4809* (2013.01);
(Continued)

(58) Field of Classification Search
CPC ........ A61M 2230/005; A61M 2230/04; A61M 2230/40; A61M 2230/63; A61M 2021/0022; A61M 2021/0027; A61M 2021/0083; A61M 21/00; A61M 2205/505; A61B 5/4809; A61B 5/4812; A61B 2562/0219; A61B 5/0205; A61B 5/02055; A61B 5/11; A61B 5/1118; A61B 5/6802; A61B 5/6892; A61B 5/6898;
(Continued)

(56) References Cited

U.S. PATENT DOCUMENTS 5,008,865 A * 4/1991 Shaffer ................ H05B 39/083
368/10
6,888,779 B2 * 5/2005 Mollicone .............. H05B 47/16
368/10

(Continued)

FOREIGN PATENT DOCUMENTS

EP 2976994 A2 1/2016
JP 5300602 B2 6/2010

*Primary Examiner* — Daniel Previl
(74) *Attorney, Agent, or Firm* — Berggren LLP

(57) ABSTRACT

The present invention discusses a system and method for defining an optimal wakeup time with an alarm, which method takes into consideration at least two persons. Sleep monitoring devices, such as health rings or bed sensors, measure parameters of the sleepers, and a server determines sleeping phases from the measurement results. In that regard, skin temperature, heart rate and amount of motion can be tracked with the ring. The analysis combines at least two persons and sets rules so that no-one is preferably woken from a deep sleep phase. The determined alarm time is a given time period before the final alarm deadline. An optimal alarm time is calculated in the server, and the alarm is triggered in a mobile device, through the wearable ring, or by another alarming device or means.

13 Claims, 5 Drawing Sheets

(51) Int. Cl.
*A61B 5/00* (2006.01)
*H04W 4/80* (2018.01)
*H04W 52/02* (2009.01)
*A61B 5/0205* (2006.01)
*A61B 5/024* (2006.01)
*A61B 5/11* (2006.01)

(52) U.S. Cl.
CPC .......... *A61B 5/4812* (2013.01); *A61B 5/6802* (2013.01); *A61B 5/6892* (2013.01); *H04W 4/80* (2018.02); *H04W 52/0216* (2013.01); *H04W 52/0254* (2013.01); *A61B 5/024* (2013.01); *A61B 5/1118* (2013.01); *A61B 2562/0219* (2013.01)

(58) Field of Classification Search
CPC ..... A61B 5/7246; A61B 5/7264; A61B 5/024; G16H 40/63; G16H 20/30; G16H 50/20; G16H 50/30; G16H 50/50; G04F 10/00; G06F 19/3481; G06Q 10/109; G06Q 50/22; G08B 21/06; G09B 7/00; G11B 27/105; H04W 4/80; H04W 52/0216; H04W 52/0254; H04W 4/38

USPC ...... 340/539.12, 539.15, 286.05, 575, 573.1, 340/540, 573.7, 531, 539.1, 500
See application file for complete search history.

(56) References Cited

U.S. PATENT DOCUMENTS

| | | | |
|---|---|---|---|
| 7,515,041 B2 * | 4/2009 | Eisold | G08B 27/008 340/286.02 |
| 8,482,418 B1 * | 7/2013 | Harman | A61B 5/0002 340/573.1 |
| 2010/0152546 A1 | 6/2010 | Behan et al. | |
| 2011/0230790 A1 * | 9/2011 | Kozlov | A61B 5/4812 600/595 |
| 2012/0253220 A1 * | 10/2012 | Rai | A61B 5/4806 600/544 |
| 2014/0277255 A1 * | 9/2014 | Sabesan | A61N 1/36139 607/45 |
| 2016/0035205 A1 * | 2/2016 | Messenger | G08B 21/0453 340/539.15 |
| 2016/0151603 A1 | 6/2016 | Shouldice et al. | |
| 2018/0060507 A1 * | 3/2018 | Ning | G16H 50/30 |

* cited by examiner

Figure 5

METHOD, MOBILE DEVICE AND SYSTEM FOR OPTIMIZING WAKE-UP ALARM FOR TWO OR MORE PERSONS

PRIORITY

This application claims priority of Finnish patent application number 20185777 filed on Sep. 19, 2018 the contents of which are fully incorporated herein by reference.

TECHNICAL FIELD

The present invention relates generally to an application where wake-up alarm timing is optimized for more than one person, and to a personal device performing such analysis.

BACKGROUND OF THE INVENTION

Everyone needs sleep. A normal sleeping period can consist of sleeping phases such as REM Sleep (REM=Rapid Eye Movement), Light Sleep and Deep Sleep. Also different names and terms have been used for sleep phases but anyway the phases describe the deepness of sleep. It is also known that a normal sleep period consists of one or more cycles. A cycle can be named to start from any awakening period or from a REM sleep phase. Different phases can follow each other in each cycle in the same order. Typically, one cycle can be as follows: REM Sleep-Light Sleep-Deep Sleep-Light Sleep-REM Sleep. Phases may occur in a different order and some phases can be missed.

As the night progresses, the time spent in Deep sleep decreases and the time spent in Light and REM sleep increases, so that there is a greater proportion of Deep sleep phase earlier in the night, and a greater proportion of Light and REM sleep later in the night, particularly during the last two sleep cycles. The cycles and phases repeat regularly and they can be estimated from the previous phase or from previous nights. It is also possible to estimate sleep cycles based on user's activity during the previous day or days and sleep during the previous night or nights.

Normal wake-up happens after a light or very light sleeping phase such as REM sleep or Light sleep. It is also known that it is not easy to wake up from a deep sleep phase. If the person is forced to wake up on these phases, he/she may feel sleep inertia even in the situation when the person has slept well.

So, it is known that the best time to wake up is during light sleep phases such as REM sleep or Light sleep. If the person is not forced to wake up, waking up will most probably happen during these phases. If the person is using an alarm clock or an alarming wake-up device, the timing may not be optimal. And if the person is sleeping with his/her partner or mate or with a child or any other person or persons in the same room, the wake-up time and alarming for one person may be non-optimal for other people in the room.

US patent application publication "Shouldice", US 2016/0151603, discloses a processing system which uses methods to promote sleep. It includes a non-contact motion sensor in a bedside position. Sleep stages and "body scores" can be recorded, evaluated and displayed for the user. Ambient or environmental conditions can be monitored as well. The system generates sleep advice from sleep and environmental information from one or more sleep sessions, the sleep advice promoting good sleep habits and detecting risky sleep conditions. The bedside sensor unit, smartphone and a network can be part of the system.

A Japanese publication JP 5300602 discloses an air-conditioning system which is controlled in basis of a determined sleep state of a person in the air-conditioned premises. The system includes an IR sensor for remote monitoring of the person, which takes a thermal image of the sleeping person. The body motion (magnitude and times of body movement) is tracked together with the surface temperature, and the sleep state is determined based on these parameters. The air-conditioner is controlled in turn in the basis of the determined sleep state, obviously to improve the sleeping conditions. A group of people are mentioned to be in the IR image, and it seems that the system separates the persons in the image in its analysis, and uses them in the controlling action in one-by-one basis. This document applies a wake-up stage, REM stage and four sleep depth stages.

EP 2976994 discloses a sleep assist system to monitor and assist the user's sleep, where the system comprises a bedside device positioned near the user's bed, where the bedside device comprises at least one of a loudspeaker, a light source, a microphone, a light sensor, a temperature sensor, a humidity sensor, a control unit, an air quality sensor, a display unit, a user interface. The system further comprises a first sensing unit positioned in the user's bed, this unit comprising one or more sensors adapted to sense at least pressure and/or changes in pressure exerted by the user lying in the bed. The system further comprises an additional sensor device which is in contact with the user's body, and further coupled to the bedside device. The system correlates the data obtained from both the first sensing unit and the additional sensor device.

Furthermore, the system of EP 2976994 monitors the user's sleep, assesses the user's sleep cycles and the phase of sleep cycle, and provides the user with at least one light and sound program, which is based on the assessment of the user's sleep cycles and the phase of sleep cycle. Heart rate, respiration, user's skin temperature, and snoring sounds can be detected, and environmental parameters such as the bedroom temperature. Certain assessments can be made by the system, such as a current phase of the female menstrual cycle, stiffness of the user's arteries, heart volume stroke, blood pressure, possible diagnosis of sleep apnoea. An alert to a $3^{rd}$ person may be provided in case the system is used by people with medical condition, elderly people, pregnant women, and an unexpected situation happens. The system may comprise a mobile terminal, which displays the information obtained by the bedside unit, the sensing unit and/or the additional sensor device. Feedback from the user can be given with the mobile device to adjust the system accordingly.

The prior art has still not covered the situation where the wake-up time is optimized for a group of people sleeping in the same room or otherwise in the same space. Also the IR sensors and remote movement sensors are just able to track externally visible movements and surface temperatures of the sleeper's body.

SUMMARY OF THE INVENTION

The present invention introduces a method for defining an optimal wake-up time with an alarm, which method takes into consideration at least two persons. The method is characterized in that the method comprises the steps of:

determining a wake-up deadline time and a time window for the alarm ending at the wake-up deadline time, and determining sub-period lengths for the analysis which subsequent sub-periods together form the determined time window, receiving a first set of measurement data related to a first person from a sleep monitoring device of the first person, determining sleep modes of the first person prior to the wake-up deadline time based on the first set of measurement data, receiving a second set of measurement data related to a second person from a sleep monitoring device of the second person, determining sleep modes of the second person prior to the wake-up deadline time based on the second set of measurement data, comparing sleep modes of the first person and the second person continuously within each sub-period during the time window for the alarm, and when the comparison gives a first positive analysis result within a specific sub-period, selecting the alarm time at the specific sub-period and triggering the alarm at the optimal wake-up time for the at least two persons.

In an embodiment of the invention, the sleep modes are determined from a group of the following sleep phases: deep sleep, light sleep, REM sleep and awake state.

In an embodiment of the invention, the sleep modes are determined as likelihood of one or more of the following sleep phases: deep sleep, light sleep, REM sleep and awake state.

In an embodiment of the invention, the time window for the alarm is 30 minutes or 45 minutes.

In an embodiment of the invention, the sub-period length is from 30 seconds to ten minutes.

In an embodiment of the invention, the set of measurement data related to a person comprises at least one of motion, skin temperature and heart rate of the person.

In an embodiment of the invention, the sleep phase of the person is determined by motionless time periods within the sub-period length, where the time periods are of temporal lengths of one to five seconds.

In an embodiment of the invention, the alarm time is selected at a sub-period when all considered persons are likely not in deep sleep, by considering the likelihoods.

In an embodiment of the invention, also other sleep information can be used for selecting an optimum alarm time, comprising a currently obtained amount of sleep compared to a typical need of a person.

In an embodiment of the invention, a single mobile device analyzes the measurement data of all considered persons.

In an embodiment of the invention, a sleep monitoring device measures the data, analyses the measured data, receives data or analyzed data from another sleep monitoring device, decides an alarm time, and makes an alarm or sends an alarm triggering signal to another alarming device.

According to a second aspect of the invention, it introduces a mobile device for defining an optimal wake-up time with an alarm, taking into consideration at least two persons, the mobile device comprising at least one application suitable for collect and analyze data from a sleep monitoring device worn by a person. The mobile device is characterized in that it is configured to:
 collect data from at least one sleep monitoring device,
 send data to a cloud service, and
 receive data from the cloud service to set a common alarm to all considered persons.

In an embodiment of the invention, the mobile device sends an alarm information to at least one of the sleep monitoring devices for triggering the alarm in corresponding sleep monitoring device(s).

According to a third aspect of the invention, it introduces a system for defining an optimal wake-up time with an alarm, which system takes into consideration at least two persons, wherein the system comprises:
 a sleep monitoring device worn by each of the persons,
 at least one mobile device in connection to the sleep monitoring devices, wherein the at least one mobile device is connected to a cloud service, and
 a server connected to the cloud service.

The system is characterized in that the system is configured to perform the method according to any of its embodiments so that
 parameter determinations are configured to be inputtable to the mobile device,
 sleep monitoring devices are configured to measure physical and/or biological parameters of each person, and
 sleep mode determinations, comparisons and alarm time selections are configured to be performed in the server.

In an embodiment of the invention, the alarm is configured to be triggered in the mobile device or in at least one of the sleep monitoring devices by a tactile manner using a piezoelectric element in an alarming means.

In an embodiment of the invention, the sleep monitoring device is a device or at least one sensor installed to a bed, or a wearable device by the person.

In an embodiment of the invention, the wearable device is a ring or a wrist device.

In an embodiment of the invention, the wearable devices are configured to measure each person with a direct skin contact.

In an embodiment of the invention, motion of the person is configured to be measured with an accelerometer within the wearable device.

In an embodiment of the invention, motion data is configured to be sent through a Bluetooth interface for each sub-period, and in case of no sent motion data within a given sub-period, it is configured to be interpreted as no motion of a person for the given sub-period.

BRIEF DESCRIPTION OF THE DRAWINGS

FIG. 5 is an illustration of exemplary sleep phases and cycles for two persons and six nights in a data table format, in accordance with an embodiment of the present invention.

DETAILED DESCRIPTION OF THE INVENTION

Figure 1:
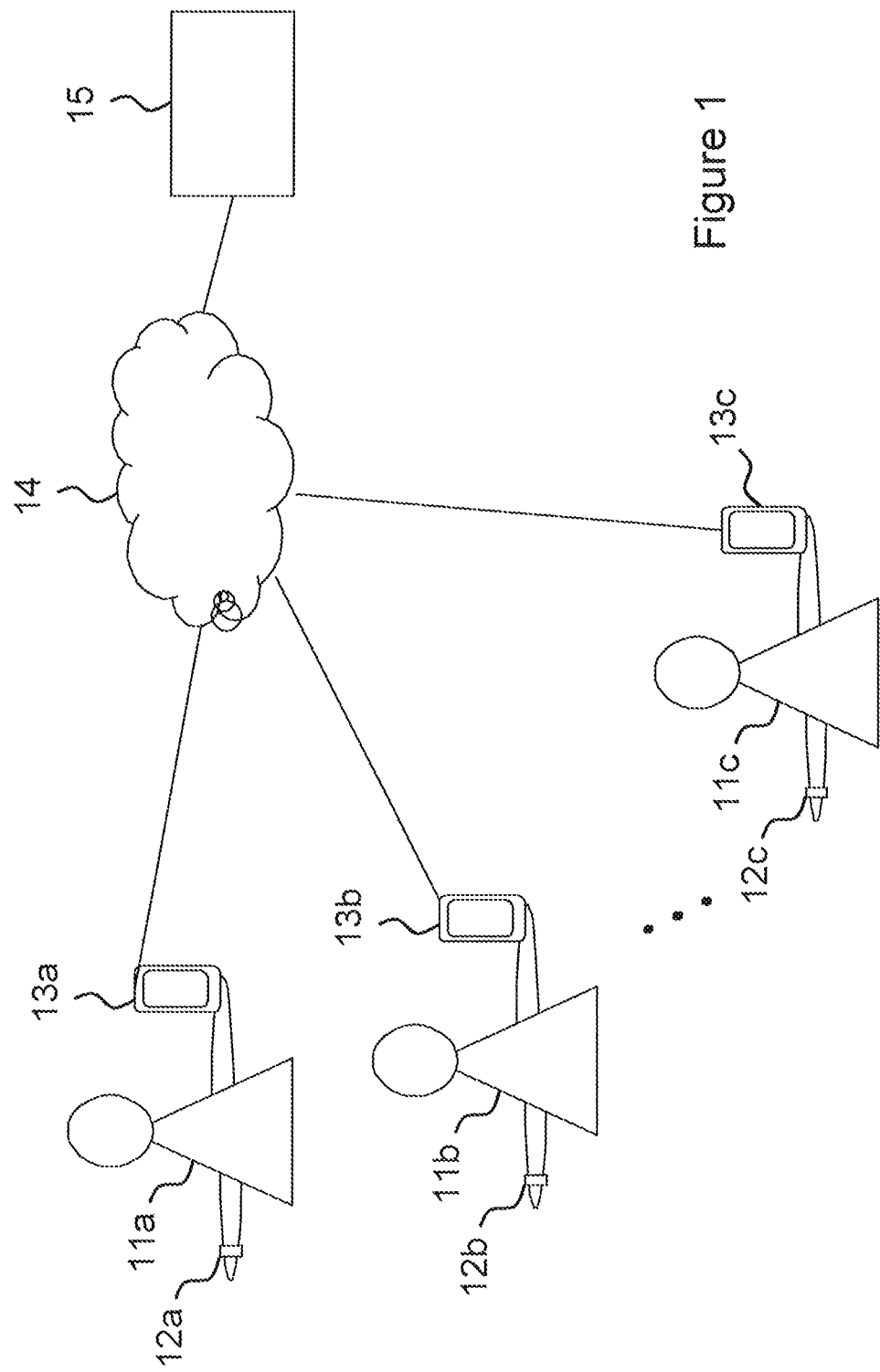
FIG. 1 is a schematic illustration of a system for providing an optimal alarm, in accordance with an embodiment of the present invention.

The following detailed description illustrates embodiments of the present invention and some ways in which they can be implemented.

The present invention introduces a method for defining the optimum wake-up time with an alarm to take into consideration two or more persons related to the alarm.

The present invention also introduces a corresponding system for defining the optimum wake-up time with an alarm to take into consideration two or more persons related to the alarm.

The method and system provide clear advantages for the user(s) to define an optimum wake-up time and to set an alarm so that it takes into consideration the sleep phases of at least one other person.

The method and system also provide clear advantages for the user(s) to define an optimum wake-up time and to set an alarm so that it takes into consideration the sleep phases of at least one other person to minimize the possibility for alarming the first user during the time, when it disturbs the other user the most.

In a first embodiment of the invention, the system comprises the following parts, devices and their characteristics. A user is provided with a wearable device, such as a wearable ring or a wrist device, and furthermore, he/she is provided with a mobile device, such as a smartphone or tablet.

In a second embodiment of the invention, a wearable device is replaced by at least one bed sensor. The bed sensor(s) can be installed under the top sheet of the bed, or within the blanket or pillow or within the mattress of the bed. One option is to place the bed sensor(s) right under the top fabric of the mattress. The sensor(s) are preferably chosen to have a suitable form and thickness so that the sleeper is not distracted by the tactile experience of the sensors themselves, not even through the sheets or fabrics right under the sleeper's body. This is possible e.g. by an embedded placement within the mattress itself without any extruding parts from the regular design (i.e. form) of the mattress. Generally, it can be said in the second embodiment, the system comprises at least one sensor installed to a bed, or to another kinds of sleeping "platforms" such as to a sleeping bag or to a hammock. Similarly as in the ring embodiment, the at least one bed sensor(s) are configured to detect the motion, heart rate and/or breathing rate of the user (i.e. the sleeping person).

Generally, both the wearable device (such as a ring) and the bed sensors can be called as a sleep monitoring device. The sleep monitoring device is of course an electronic device in both these aspects of the device.

The sleep monitoring device is connected wirelessly to the mobile device; e.g. by Bluetooth, Bluetooth LE, modem, any low power radio, Wi-Fi, or the like, technology.

The mobile device is connected to the web or cloud by a 3G, 4G LTE, or 5G or Wi-Fi or by any other wireless communication radio and protocol.

A server is connected to the cloud; e.g. by wired ethernet, wireless 3G, 4G LTE, or 5G or Wi-Fi or by any other wireless communication radio and protocol.

In the first embodiment, the sleep monitoring device comprises:
  sensors: with capability to measure motion, and optionally also temperature and/or heart rate
  microcontroller, and memory
  communication means for connecting to the mobile device
  optionally an alarming means which may comprise a piezo element In the first embodiment, the sleep monitoring device measures motion, and optionally also temperature and/or heart rate to define sleep phases of the user. The measurement data is sent to the mobile device in predetermined time instants, e.g. in every 30 seconds, but the range can vary between 10-120 seconds.

The mobile device of the system receives input from the user. The user input comprises an alarm time, and a window time for the alarm (for example ±15 minutes), and if not given, the default can be for example ±15 minutes. Furthermore, the user input comprises information of users which are needed to be followed related to the alarm. In this regard, the mobile device can inform about the devices or users nearby the first user by e.g. a standard Bluetooth searching option. Otherwise or in addition to that, the mobile device can communicate with the cloud or server to ask users related to the first user and propose a list of possible users to be followed.

Furthermore, the mobile device receives and analyses the data, and defines the sleep phase, for instance in every 30 seconds but the range may vary between 10-120 seconds. In an alternative embodiment, the sleep phase can be defined in the sleep monitoring device instead. In a yet alternative embodiment, the sleep phase can be defined in the server instead.

Furthermore, the mobile device sends the sleep phase data to the cloud or web (i.e. a server in a network). Thereafter, the mobile device receives related sleep phases of the other users, which are to be followed, from the web, cloud or server. Thereafter, the mobile device analyses the sleep patterns of different users. After that, the mobile device is able to define an alarm time. When the appropriate alarm time is reached, the mobile device triggers the alarm, which results in that the mobile device sends an alarming control signal to the sleep monitoring device, and then, the sleep monitoring device makes the alarm and thus, wakes up the user. Alternatively, the mobile device itself may trigger the alarm by itself (i.e. as a smartphone alarm from its clock app). In a further alternative solution, the device performing the alarm (i.e. the alarming device) can be e.g. a radio or a light source connected in a wired or wireless manner to a mobile device. In this sense, a radio program, a preselected piece of music or switched-on light(s) act as alarming means. Also other devices can be connected to the mobile device or to the device performing the alarm, such as a coffee machine, motorized curtains, and home automation devices such as heaters, coolers and lights. These can be considered as auxiliary (additional, supportive) alarming means or other useful home apparatuses linked to the morning routines in a way or another.

In the first embodiment of the system, a server is configured to perform the following steps and actions (a part of them are optional):
  the server keeps record of different users using a sleep monitoring device
  the server receives data from different mobile devices connected to different sleep monitoring devices
  the server can analyze data
  the server can also analyze sleep data from different users
  the server can analyze and define sleep patterns of a user
  the server can define the alarm time
  the server can send the defined alarm time to a mobile device, and the mobile device makes the actual alarm or triggers a wearable device or other device(s) to make the actual alarm The general system structure is illustrated in FIG. 1, showing a group of users i.e. sleepers in the same room who are subject to the analysis according to the invented method. The system comprises N users (just three of them shown, users 11*a*-11*c*). Each user 11*a*-11*c* has a sleep monitoring device 12a-c which is an electronic device. In this example, the sleep monitoring device is a personal wearable device 12a-c, and each user also has a personal smartphone 13a-c. The smart phones 13a-c or other smart devices are in connection to the network, represented here as cloud 14. As part of the network, there is a server 15 which can be a computer within the user's own premises (e.g. at home) or a computer within the service provider's premises. Also, there is a connection between each pair of a wearable device 12a-c and a smart phone 13a-c, and thus, the wearable devices 12a-c are all connected to the network, for transferring the measurement results from all users 11a-c to the server 15, and for other needed information transfer.

Next, an example of a night comprising sleep cycles and their sub-phases with different deepness of sleep, are depicted for a single person. The bed time is set to start at 24:00 pm, and the bed time is set to end at around 7:15 am. The uppermost horizontal line shows the time periods when the person is awake, the next line presents when the user is in REM sleep, the third line from the top represents the times when the user is in Light sleep, and the bottom line shows times when the user has reached the Deep Sleep phase. Thus, these four levels of sleep/awake status have been determined here.

Figure 2:
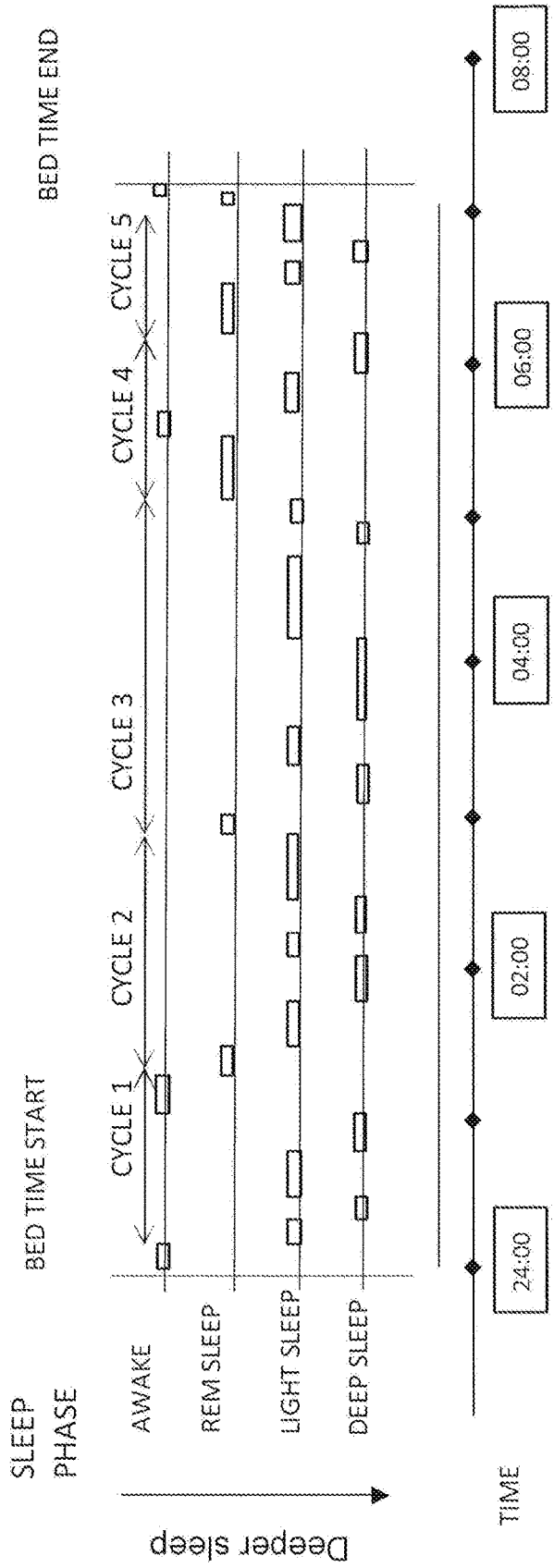
FIG. 2 is an illustration of exemplary sleep phases and cycles for a person for one night, in accordance with an embodiment of the present invention.

The sleep cycles have been determined so that their mutual seam moments occur when the sleep is in its lightest phase. In practice, the moment between adjacent cycles occurs during either in the REM sleep phase or during the Awake state. In the example depicted in FIG. 2, the first sleep cycle ends when the person falls asleep the second time (after a deep sleep phase) and thus enters a REM sleep phase there; the second sleep cycle ends when a second REM sleep phase starts; the third sleep cycle ends when a third REM sleep phase starts, and so on, until in the end of the fifth sleep cycle, the user wakes up near the pre-specified bed time end. As it can be seen during the fourth sleep cycle, there is a brief awaken period within the cycle but the cycle is still determined between the starts of consequential REM sleep phases where there is a deep sleep phase between such REM sleep phases. The cycles may well be of different temporal length, as is the case in this example. Of course, any other number of cycles is possible within a single night. Also the length of the needed sleeping time varies with different people, so thus, the bed time start and bed time end can be individually determined in the server.

As already discussed in the background, the amount of deep sleep is important for the wellbeing of the person, while the REM sleep offers the times of dreaming for the sleeper. It is a worrying sign if there is excessive amount of light sleep or awaken periods within the night. These issues can be tracked and possibly corrected when the user has the information available, like the way presented in FIG. 2.

Next, analysis of a sleep phase can be performed as in the following example.

Simple rules can be determined for defining different phases of sleep. These rules can be defined by using measurable characteristics obtained from the sleeping person him-/herself. Such characteristics may involve the skin temperature, activity (movement) of the sleeper and the heart rate of the sleeper. These parameters are also measurable directly with a sleep monitoring device without a need for additional sensoring e.g. elsewhere in the bedroom premises (like in prior art). It is emphasized that the following parameter limits are mere examples, and also some other values and ranges can be applied in determining the sleep phases. In an embodiment, it is possible to tune these parameter values by updating them in the memory which is accessible by the server.

The Awake phase can be determined as follows:
  skin temperature T: T>34 (the unit is Celsius degrees: ° C.)
  activity A: A>9 (the unit is seconds of user motion per minute)
  heart rate HR: HR>65 (the unit is beats per minute)

The REM Sleep can be determined as follows (with same units as in the above):
  skin temperature T: T<34
  activity A: 2<A<10
  heart rate HR: 55<HR<70

The Light Sleep can be determined, correspondingly:
  skin temperature T: T<33
  activity A: 0<A<3
  heart rate HR: 50<HR<65

Finally, the Deep Sleep can be determined to occur within the following parameter ranges:
  skin temperature T: T<32
  activity A: A<1
  heart rate HR: HR<60

In practice, all three conditions can be checked simultaneously or in serial manner in order to determine the specific sleep phase for the sleeping person.

In practice and in the simplest case, the rule can be based even on only one parameter, for example activity, after the earlier sleep phases have been properly defined for the particular sleep period. This uses the order and serial nature between the different sleep phases in the analysis.

For example, at first, all three parameters are followed and the first sleep phases have been defined based on the three parameters, but after the first light sleep or deep sleep period, the activity is only followed and the next sleep phases are defined based on the activity count only as the rule says in the above.

The above three parameters are examples of physical and biological parameters measurable from a person.

In an example according to the invention, the alarm time can be defined as follows. This is a first example of the alarm time definition.

Rules of the first example of defining the alarm time for a bedroom comprising two sleeping persons:
1. First check that current time is in the range of the time window of the alarm.
2. If any person is in a Deep sleep phase, then no alarm.
3. If both persons are in the REM sleep phase, do the alarm.
4. If at least one person is in light sleep; check the sleep phase trend for the users, so that:
   1. if the first person is going to lighter sleep, and another is going to deeper sleep, do the alarm.
   2. if the first person is going to lighter sleep, and another is going to lighter sleep or being in the same status, postpone the alarm.
   3. if both persons are going to deeper sleep, do the alarm.
5. If no good time during the time window of the alarm, set alarm at the end of the time window i.e. at the alarm deadline.

Figure 3:
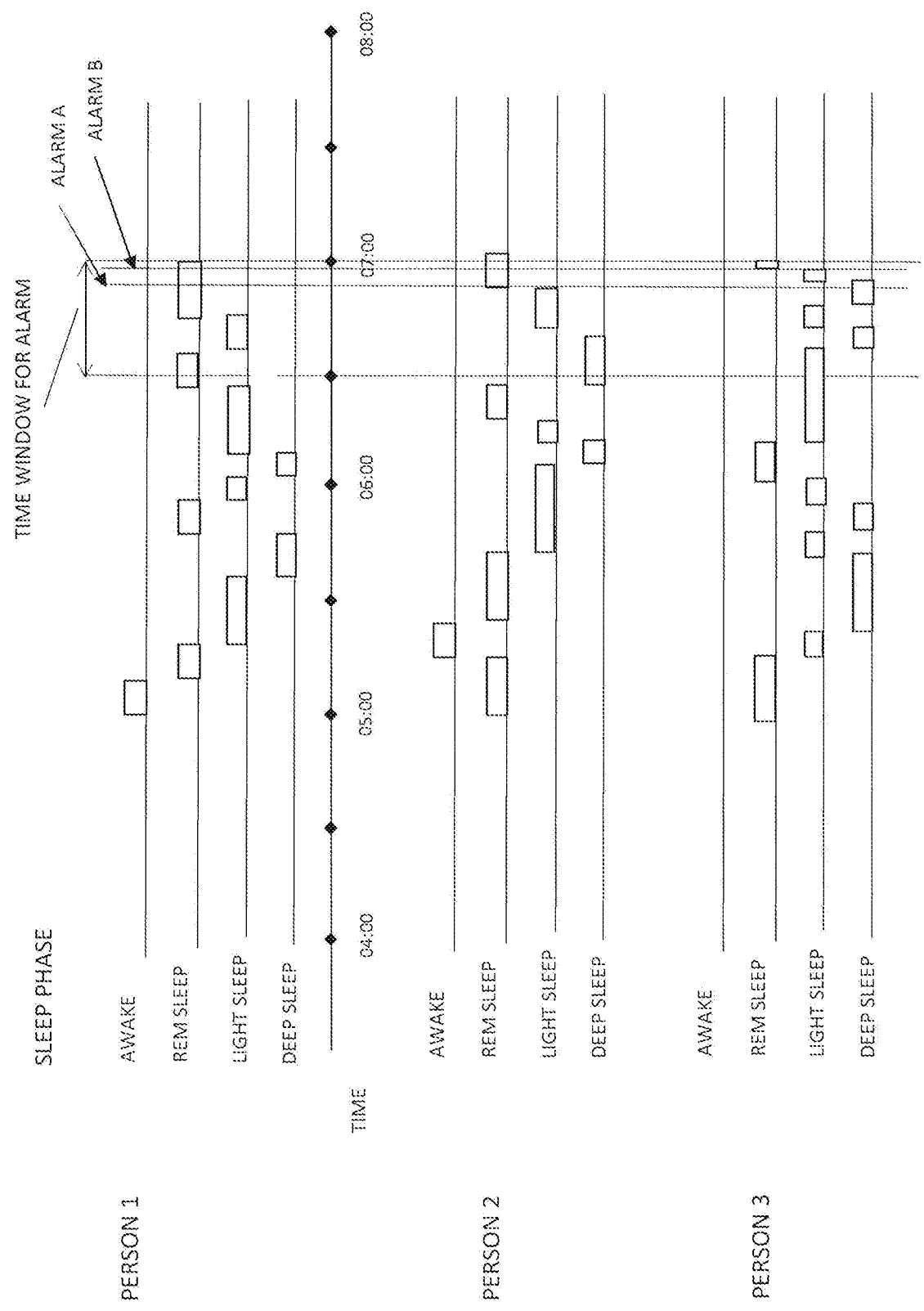
FIG. 3 is an illustration of exemplary sleep phases and cycles for three persons, in accordance with an embodiment of the present invention.

This example is explained with referring to the graph of FIG. 3. It also includes a third sleeping person, see the following.

If only person 1 and person 2 are analysed (the two-person embodiment), the alarm time A is selected as an optimum time for the alarm. Both persons are not in deep sleep phase then, and both persons are in the REM sleep phase (person 2 just entered it).

If person 1, person 2 and person 3 are analysed (the three-person embodiment), the alarm time B is selected as an optimum time instant for all three sleepers. All the persons are not in a deep sleep phase, and all persons are in an REM sleep phase (person 3 just entered it). The analysis algorithm may detect e.g. in the instant of A that the sleep phases of person 2 and person 3 are going to be lighter, so the algorithm will postpone the alarm until all three persons 1, 2 and 3 are in the REM sleep phase. Time B is the first instant within the time window for alarm, when this condition is fulfilled.

In an alternative solution, the alarm time can be defined as follows. This is a second example of the alarm time definition.

In this embodiment, a motion-based method is used for defining the sleep level and an optimal alarm time.

The motion sensing can be used as a suitable indication for a deepness of sleep. During the deep sleep, the likelihood of motion of the user is lowest, and it is second lowest during a lighter phase of sleep, like for example during the REM sleep.

In this embodiment, it is desired to detect when a person or persons are not in the deep sleep phase or the likelihood to be in the deep sleep is low, or alternatively, lower than in the previous measurement instant. With "low", we mean e.g. probabilities equal or less than 20%.

At first, a sleep monitoring device with a motion sensor, for example an accelerometer, detects motions of the user. This applies for every person in the room through their individual sleep monitoring devices. The motion detection detects if the motion of the user is exceeding a set threshold value; for example 0.05 g with using an accelerometer. In more detail, the motion detection algorithm in a sleep monitoring device classifies every second for two classes; namely a motion second or a motionless second. The second is classified to be a motion second, if the motion signal exceeds the threshold value during the second, and if it is not exceeding it, the second is classified as a motionless second. Next, the motion algorithm in the sleep monitoring device counts the motion seconds during each minute (maximum being 60 and minimum is 0).

Next, the algorithm in the sleep monitoring device may define the sleep level or likelihood of a certain sleep level for the person for each minute. In case there are zero motion seconds detected during the minute, there is a high likelihood of deep sleep. If there is one motion second detected during the minute, there is a medium likelihood of deep sleep. Finally, if there are two or more motion seconds detected during the minute, there is a low likelihood of deep sleep. This is the same as a high likelihood of the person being in light sleep (comprising the REM sleep) or awake.

The sleep monitoring device may send the sleep level or the likelihood of a certain sleep level of the user to the mobile device.

In one applicable embodiment, the sleep monitoring device counts motion seconds and it can send the number of motion seconds to a mobile device once in every minute, for example using a Bluetooth connection (BT). If the number of motion seconds is zero, the sleep monitoring device may not send any data and the mobile device is recognizing that no signal is received for this minute from the sleep monitoring device, so the minute was motionless. The power consumption of the sleep monitoring device can be minimized this way. Also, the data of number of motion seconds can be sent as minimum data amount using known BT protocol properties to minimize power consumption of a BT transceiver in the sleep monitoring device.

Next, the mobile device sends the data to the cloud service in every minute or in any other specified time intervals from 10 seconds to 10 minutes. The cloud service also receives another person's sleep data from another mobile device and a sleep monitoring device in every minute or in any other specified time intervals. The cloud service will now analyze sleep levels or likelihood of sleep levels of the two persons in every minute or in any other specified time intervals. The method is then determined to judge when to wake up two or more persons based on their sleep levels or likelihoods of deep sleep.

Figure 4:
FIG. 4 is an illustration of steps of a method for determining an optimum alarm time, in accordance with an embodiment of the present invention.

FIG. 4 illustrates steps of a method for determining an optimum alarm time, in accordance with an embodiment of the present invention.

In the first step of the method, the information which is related to user's preference for wake-up time, is collected 1202. This means that the user may specify that a desired last time for waking up is e.g. at 7:30 am, just to show an exemplary time period.

In the second step, a time window is generated for the wake-up time 1204. For example, it may be determined that a desired time window is during the last 45 minutes before the alarm deadline (i.e. the desired last time for the wake-up), meaning that the time window is between 6:45-7:30 am.

In the third step, information is collected also about another user (the $2^{nd}$ person in the bedroom), which is related to the wake-up time and possible alarm 1206. This means that the second person may also specify a desired final time limit for his/her wake-up time. And after that, the time window is specified also for the second user. In an embodiment, the alarm deadline and the desired time window are set to be the same as with the first person, unifying the desired input parameters among the users in the same bedroom.

In the fourth step, sleep parameters are measured for determining sleep phases and cycles of the first user 1208.

Correspondingly in the fifth step, the same is performed for the second user, i.e. sleep parameters are measured for determining sleep phases and cycles of the second user 1210.

Now the core step of the invention happens in the sixth step of the method, where a parameter value is determined which describes an optimum wake-up time within the time window so that it takes into consideration both above users 1212. The logic behind the determination has been discussed earlier in the context of FIG. 3.

Finally, in the seventh step of the method, the alarm is activated in the determined optimal wake-up time in order to wake up the first person 1214. If desired, the waking up can be set simultaneously for both persons in the room, is there are two sleepers in the room. This step concludes the invented method in this embodiment.

Figure 5:
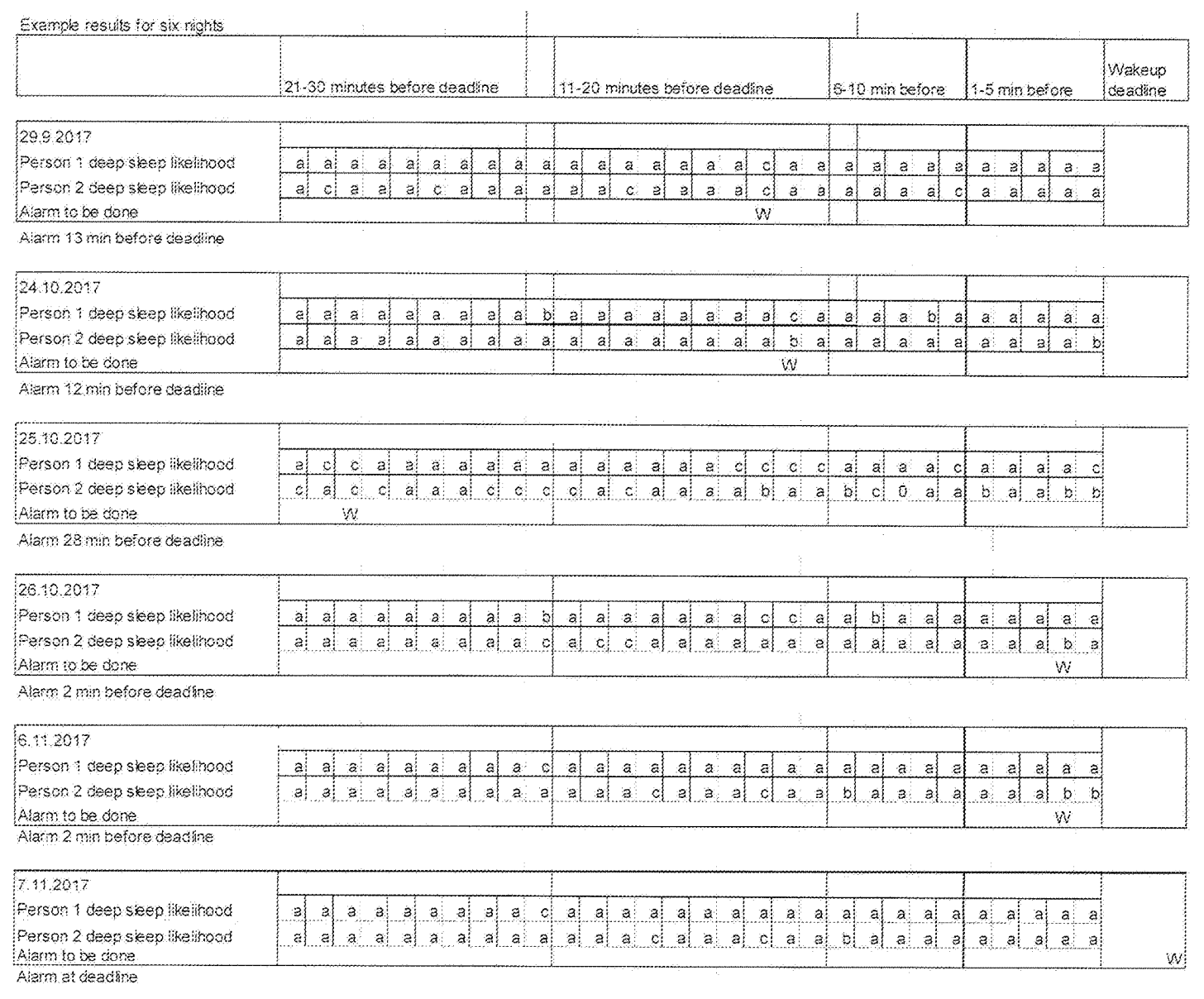

FIG. 5 shows examples of six nights of collected and analyzed sleep data. In the example, these are collected from three different time periods, the first one comprising 29 Sep. 2017, the second one comprising three days (=nights) on 24-26 Oct. 2017, and the third time period comprising two days between 6-7 Nov. 2017. The data table comprises sleep data of two persons, the wake-up deadline for the alarm, and the actually triggered alarm time (i.e. "alarm to be done"). The horizontal axis means the passed time (i.e. a time window usually in the morning).

The set alarm deadline (i.e. the wake-up deadline) is on the right column. The previous 30 minutes are divided into one-minute columns with four phases; 21-30 minutes before the wakeup deadline, 11-20 minutes before the wakeup deadline, 6-10 minutes before the wakeup deadline, and 1-5 minutes before the wakeup deadline.

The data collected from both sleep monitoring devices of the two users are shown as markings "a", "b" and "c", where
"a" means "a high likelihood of deep sleep"
"b" means "a medium likelihood of deep sleep"
"c" means "a low likelihood of deep sleep".

It can be alternatively specified that "a" means the Deep Sleep phase, "b" means the Light sleep phase and "c" means either the REM sleep phase or the Awake state of the person.

The algorithm in the cloud service will analyze and obtain as a result a suitable alarm time so that it suits optimally both persons simultaneously.

The rule can be the same for each phase or the rules can be different in each phase. For example, the rules to judge the alarm time for each phase can be as in the following:
1. 21-30 minutes before deadline: generate wake-up if everyone have a low likelihood of deep sleep during the same minute.
2. 11-20 minutes before deadline: generate wake-up if one of the persons has a low likelihood of deep sleep and the others have at most a medium likelihood of deep sleep during the same minute.
3. 6-11 minutes before deadline: generate wake-up if everyone have at most a medium likelihood of deep sleep during the same minute.
4. 1-5 minutes before deadline: generate wake-up if only just one of the persons has at most a medium likelihood of deep sleep.
5. At the wakeup deadline time, we must generate a wake-up alarm in any case.

This way the wake-up time is selected intelligently to ensure a smooth and optimal waking up for both (all) of the sleepers in the same room, within a predetermined time period before the wake-up deadline.

Based on the rules, the selected alarm time is shown as "W" in FIG. 5.

For example, at the day/night of 29 Sep. 2017 (29.9.2017), person 1 is almost the whole 30 minutes in mode "a" meaning "a high likelihood of deep sleep", but only one single minute at 13 minutes before the alarm deadline in mode "c" meaning "a low likelihood of deep sleep". Person 2 is also most of the time in mode "a" and five one-minute periods in mode "c". The alarm criteria fulfil at 13 minutes before the wakeup deadline, when both persons are in mode "c". The alarm is triggered then.

For a further example, at the day/night of 24 Oct. 2017 (24.10.2017), person 1 is almost the whole 30 minutes in status "a" meaning "a high likelihood of deep sleep", except two one-minute periods in "b" and a single one-minute period in "c". Person 2 is also most of the time in "a", except two one-minute periods in "b". The alarm criteria fulfil at 12 minutes before the wakeup deadline, when person 1 is in "c" and person 2 is in "b". The alarm is triggered then.

For a further (third) example, at the day/night of 25 Oct. 2017 (25.10.2017), the alarm criteria fulfil at 28 minutes before the wakeup deadline, when person 1 is in "c" and person 2 is in "c", too. The symbol "0" (eight minutes before the wakeup deadline for person 2) means a loss of connection to the sleep monitoring device in that particular minute.

For a further, fourth, example, at the day/night of 26 Oct. 2017 (26.10.2017), the alarm criteria fulfil at 2 minutes before the wakeup deadline, when person 1 is in "a" and person 2 is in "b".

For a further, fifth, example, at the day/night of 6 Nov. 2017 (6.11.2017), the alarm criteria fulfil also at 2 minutes before the wakeup deadline, when person 1 is in "a" and person 2 is in "b". The alarm is set to trigger in the first instance when the criteria are fulfilled, thus the alarm is triggered at 2 minutes before the wakeup deadline, and not at 1 minute before the wakeup deadline.

Finally, for a further, sixth, example, at the day/night of 7 Nov. 2017 (7.11.2017), the alarm criteria do not fulfil in any time within the 30 minutes period before the wakeup deadline, so the alarm will be triggered at the wakeup deadline (i.e. 0 minutes before the wakeup deadline, to be precise).

Also other sleep information can be used for selecting an optimum alarm time. For example, phase 2 could be split to two halves so that during the first five minutes we would generate wake-up only, if the person, who has got the smallest amount of sleep compared to his/her typical need, would have a low likelihood of deep sleep and the others at most a medium likelihood of deep sleep. During the second split half, the method can work as described above in rule no. 2.

It is also possible that another person's sleep data is sent to the first person's mobile device, and the first person's mobile device or its apps will analyze the sleep levels of the two persons to judge, when to wake up two or more persons based on their likelihood of deep sleep.

As alternative parameter example, the time window for the alarm can be selected as any suitable temporal length. While the above example discusses the time window of 45 minutes, it can also be selected as 30 minutes.

Although we have discussed in FIG. 5 the sleep phases in each minute, this temporal length can be alternatively between 30 seconds and 10 minutes. Also in the analysis of motionless seconds within a minute, the motionless periods can be tracked in time periods of 1-5 seconds (as selected between this range) while the total analysis period can be between 30 seconds and 10 minutes (as selected as well) instead of just 1 minute.

In a main embodiment, the sleep monitoring device is a small, ring-shaped health monitoring device, i.e. a ring comprising a vast amount of intelligence. Still, a wrist device can be used as well.

In an embodiment, the alarm is configured to be triggered in the mobile device or in at least one of the sleep monitoring devices by a tactile manner, e.g. through creating a vibrational movement. In case the sleep monitoring device is a ring or a wrist device, this is a practical and gentle way to wake up the persons, and even possibly to just wake up a single person through vibrating only a single ring, as a triggered alarm.

The advantages of the invention are various. The present invention helps couples, people sleeping with children or any other group of people sleeping in the same room to find an optimal waking up time, where no-one is preferably woken from the deep sleep state. The invention thus improves the activity levels of people in the morning and later in the day, because they are woken in a reasonable time within their sleeping cycle. The invention optimizes the alarming time for two, three and even more persons simultaneously, which has not been much discussed in prior art solutions. The use of a health measurement ring as the sleep monitoring device makes the measurement very practical and less disturbing. However, the ring gives a possibility to wake up a single person in the best case, and to wake up people with tactile (vibrational) techniques, thus not waking the others up in that situation (of course requiring quiet and attentive behavior and actions from the person waking up in a 2-person bedroom). An app in the smart phone makes the parameter insertions easy. The system also gives valuable feedback of each person's sleeping habits. This might even reveal some ground reasons e.g. for excessive tiredness of people during the day; by assisting such person to a professional examination, e.g. to a doctor, the feedback graphs of the sleeping cycles and lack of deep sleep may reveal a sickness or a mental stress situation of the patient.

A main advantage for the intelligent alarm creation is that people who have some freedom in their waking up time, will wake up with less tiredness, because optimally, the system won't wake up anyone in their deep sleeping phase. The deadline for the wakeup time, i.e. the alarm deadline, is of course a good feature of the invention so that people won't be late from their work or from other clock-bound commitments.

The present invention is not restricted merely to embodiments presented above but it may vary within the scope of the claims.

The invention claimed is:

1. A method for defining an optimal wake-up time with an alarm, which method takes into consideration at least two persons, wherein the method comprises the steps of:
    determining a wake-up deadline time and a time window for the alarm ending at the wake-up deadline time, and determining sub-period lengths for an analysis which subsequent sub-periods together form the determined time window,
    receiving a first set of measurement data related to a first person from a sleep monitoring device of the first person,
    determining sleep modes of the first person prior to the wake-up deadline time based on the first set of measurement data,
    receiving a second set of measurement data related to a second person from a sleep monitoring device of the second person,
    determining sleep modes of the second person prior to the wake-up deadline time based on the second set of measurement data,
    comparing sleep modes of the first person and the second person continuously within each sub-period during the time window for the alarm, and when the comparison gives a first positive analysis result within a specific sub-period,
    selecting the alarm time at the specific sub-period and triggering the alarm at the optimal wake-up time for the at least two persons, wherein
    determining the sleep modes as likelihood of one or more of the following sleep phases: deep sleep, light sleep, REM sleep and awake state,
    the sub-period length is from 30 seconds to ten minutes,
    the set of measurement data related to a person comprises at least motion of the person, where the sleep phase of the person is determined by motionless time periods within the sub-period length, where the time periods are of temporal lengths of one to five seconds,
    the sleep monitoring device is a ring or a wrist device wearable by the person, and
    sending motion data through a Bluetooth interface for each sub-period, and in case of no sent motion data within a given sub-period, this is interpreted it as no motion of a person for the given sub-period.

2. The method according to claim 1, wherein the sleep modes are determined from a group of the following sleep phases: deep sleep, light sleep, REM sleep and awake state.

3. The method according to claim 1, wherein the time window for the alarm is 30 minutes or 45 minutes.

4. The method according to claim 1, wherein the set of measurement data related to a person comprises at least one of motion, skin temperature and heart rate of the person.

5. The method according to claim 1, wherein the alarm time is selected at a sub-period when all considered persons are likely not in deep sleep, by considering the likelihoods.

6. The method according to claim 1, wherein also other sleep information can be used for selecting an optimum alarm time, comprising a currently obtained amount of sleep compared to a typical need of a person.

7. The method according to claim 1, wherein a single mobile device analyzes the measurement data of all considered persons.

8. The method according to claim 1, wherein a sleep monitoring device measures the data, analyses the measured data, receives data or analyzed data from another sleep monitoring device, decides an alarm time, and makes an alarm or sends an alarm triggering signal to another alarming device.

9. A system for defining an optimal wake-up time with an alarm, which system takes into consideration at least two persons, wherein the system comprises:
    a sleep monitoring device worn by each of the persons,
    at least one mobile device in connection to the sleep monitoring devices, wherein the at least one mobile device is connected to a cloud service, and
    a server connected to the cloud service, wherein the system is configured to perform the method according to any of claims 1-8 so that
    parameter determinations are configured to be inputtable to the mobile device,
    sleep monitoring devices are configured to measure physical and/or biological parameters of each person, and
    sleep mode determinations, comparisons and alarm time selections are configured to be performed in the server.

10. The system according to claim 9, wherein the alarm is configured to be triggered in the mobile device or in at least one of the sleep monitoring devices by a tactile manner using a piezoelectric element in an alarming means.

11. The system according to claim 9, wherein the sleep monitoring device is a device or at least one sensor installed to a bed, or a wearable device by the person.

12. The system according to claim 11, wherein the wearable devices are configured to measure each person with a direct skin contact.

13. The system according to claim 11, wherein motion of the person is configured to be measured with an accelerometer within the wearable device.

* * * * *